US008805492B2

(12) United States Patent  (10) Patent No.: US 8,805,492 B2
Chan  (45) Date of Patent: Aug. 12, 2014

(54) METHOD AND APPARATUS FOR DELIVERING COMBINED ELECTRICAL AND DRUG THERAPIES

(75) Inventor: Gregory W. Chan, Fairfield, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 734 days.

(21) Appl. No.: 12/491,957

(22) Filed: Jun. 25, 2009

(65) Prior Publication Data

US 2009/0259268 A1  Oct. 15, 2009

Related U.S. Application Data

(62) Division of application No. 10/922,650, filed on Aug. 20, 2004, now Pat. No. 7,567,841.

(51) Int. Cl.
*A61N 1/08* (2006.01)
(52) U.S. Cl.
USPC ................................. 607/3; 607/36
(58) Field of Classification Search
CPC ...................................... A61N 1/375
USPC ....................................... 607/3, 36
See application file for complete search history.

(56) References Cited

U.S. PATENT DOCUMENTS

| | | |
|---|---|---|
| 3,692,027 A | 9/1972 | Ellinwood, Jr. |
| 4,003,379 A | 1/1977 | Ellinwood, Jr. |
| 4,146,029 A | 3/1979 | Ellinwood, Jr. |
| 4,190,040 A | 2/1980 | Schulte |
| 4,281,664 A | 8/1981 | Duggan |
| 4,291,699 A | 9/1981 | Geddes et al. |
| 4,299,220 A | 11/1981 | Dorman |
| 4,544,371 A | 10/1985 | Dormandy, Jr. et al. |
| 4,556,063 A | 12/1985 | Thompson et al. |
| 4,561,443 A | 12/1985 | Hogrefe et al. |
| 4,686,987 A | 8/1987 | Salo et al. |
| 4,800,882 A | 1/1989 | Gianturco |
| 4,871,351 A | 10/1989 | Feingold |
| 4,897,987 A | 2/1990 | Spalla |
| 4,901,731 A | 2/1990 | Millar |
| 4,907,336 A | 3/1990 | Gianturco |
| 4,924,875 A | 5/1990 | Chamoun |

(Continued)

FOREIGN PATENT DOCUMENTS

| | | |
|---|---|---|
| EP | 0054138 A1 | 6/1982 |
| EP | 0347708 A1 | 12/1989 |

(Continued)

OTHER PUBLICATIONS

"U.S. Appl. No. 10/862,716, Final Office Action mailed Jul. 13, 2007", 16 pgs.

(Continued)

*Primary Examiner* — Eric D. Bertram
(74) *Attorney, Agent, or Firm* — Schwegman Lundberg & Woessner, P.A.

(57) ABSTRACT

A cardiac rhythm management (CRM) system includes an implantable medical device that delivers combined electrical and drug therapies. The implantable medical device includes a drug reservoir that is refillable after implantation. In one embodiment, the implantable medical device includes an implantable housing encapsulating a pulse generator circuit and a drug delivery device. In another embodiment, the implantable medical device includes an implantable pulse generator and an implantable drug delivery device fastened to each other.

1 Claim, 6 Drawing Sheets

(56) References Cited

U.S. PATENT DOCUMENTS

| | | |
|---|---|---|
| 4,936,281 A | 6/1990 | Stasz |
| 4,944,299 A | 7/1990 | Silvian |
| 4,983,166 A | 1/1991 | Yamawaki |
| 4,987,897 A | 1/1991 | Funke |
| 4,994,033 A | 2/1991 | Shockey et al. |
| 5,014,698 A | 5/1991 | Cohen |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,078,736 A | 1/1992 | Behl |
| 5,087,243 A | 2/1992 | Avitall |
| 5,127,404 A | 7/1992 | Wyborny et al. |
| 5,178,618 A | 1/1993 | Kandarpa |
| 5,190,035 A | 3/1993 | Salo et al. |
| 5,220,917 A | 6/1993 | Cammilli et al. |
| 5,269,301 A | 12/1993 | Cohen |
| 5,284,136 A | 2/1994 | Hauck et al. |
| 5,292,321 A | 3/1994 | Lee |
| 5,305,745 A | 4/1994 | Zacouto |
| 5,342,408 A | 8/1994 | deCoriolis et al. |
| 5,353,800 A | 10/1994 | Pohndorf et al. |
| 5,368,028 A | 11/1994 | Palti |
| 5,404,877 A | 4/1995 | Nolan et al. |
| 5,416,695 A | 5/1995 | Stutman et al. |
| 5,456,692 A | 10/1995 | Smith, Jr. et al. |
| 5,460,605 A | 10/1995 | Tuttle et al. |
| 5,496,360 A | 3/1996 | Hoffmann et al. |
| 5,499,971 A | 3/1996 | Shapland et al. |
| 5,551,953 A | 9/1996 | Lattin et al. |
| 5,556,421 A | 9/1996 | Prutchi et al. |
| 5,562,713 A | 10/1996 | Silvian |
| 5,579,876 A | 12/1996 | Adrian et al. |
| 5,586,556 A | 12/1996 | Spivey et al. |
| 5,603,331 A | 2/1997 | Heemels et al. |
| 5,607,418 A | 3/1997 | Arzbaecher |
| 5,607,463 A | 3/1997 | Schwartz et al. |
| 5,634,899 A | 6/1997 | Shapland et al. |
| 5,637,113 A | 6/1997 | Tartaglia et al. |
| 5,662,689 A | 9/1997 | Elsberry et al. |
| 5,690,682 A | 11/1997 | Buscemi et al. |
| 5,693,075 A | 12/1997 | Plicchi et al. |
| 5,693,085 A | 12/1997 | Buirge et al. |
| 5,703,125 A | 12/1997 | Bovy et al. |
| 5,720,770 A | 2/1998 | Nappholz et al. |
| 5,730,125 A | 3/1998 | Prutchi et al. |
| 5,733,313 A | 3/1998 | Barreras, Sr. et al. |
| 5,766,192 A | 6/1998 | Zacca |
| 5,775,338 A | 7/1998 | Hastings |
| 5,800,498 A | 9/1998 | Obino et al. |
| 5,814,089 A | 9/1998 | Stokes et al. |
| 5,817,131 A | 10/1998 | Elsberry et al. |
| 5,833,603 A | 11/1998 | Kovacs et al. |
| 5,836,935 A | 11/1998 | Ashton et al. |
| 5,846,218 A | 12/1998 | Brisken et al. |
| 5,876,433 A | 3/1999 | Lunn |
| 5,893,881 A * | 4/1999 | Elsberry et al. .................. 607/5 |
| 5,899,917 A | 5/1999 | Edwards et al. |
| 5,899,928 A | 5/1999 | Sholder et al. |
| 5,906,636 A | 5/1999 | Casscells, III et al. |
| 5,921,954 A | 7/1999 | Mohr, Jr. et al. |
| 5,925,066 A | 7/1999 | Kroll et al. |
| 5,944,710 A | 8/1999 | Dev et al. |
| 5,949,659 A | 9/1999 | Lesche |
| 5,967,986 A | 10/1999 | Cimochowski et al. |
| 5,972,029 A | 10/1999 | Fuisz |
| 5,991,668 A | 11/1999 | Leinders et al. |
| 6,016,443 A | 1/2000 | Ekwall et al. |
| 6,016,447 A | 1/2000 | Juran et al. |
| 6,016,448 A | 1/2000 | Busacker et al. |
| 6,053,913 A | 4/2000 | Tu et al. |
| 6,066,094 A | 5/2000 | Ben-Haim |
| 6,102,908 A | 8/2000 | Tu et al. |
| 6,104,949 A | 8/2000 | Pitts Crick et al. |
| 6,112,116 A | 8/2000 | Fischell et al. |
| 6,115,636 A | 9/2000 | Ryan |
| 6,128,526 A | 10/2000 | Stadler et al. |
| 6,140,740 A | 10/2000 | Porat et al. |
| 6,141,588 A | 10/2000 | Cox et al. |
| 6,154,675 A | 11/2000 | Juran et al. |
| 6,155,267 A | 12/2000 | Nelson |
| 6,168,801 B1 | 1/2001 | Heil, Jr. et al. |
| 6,179,824 B1 | 1/2001 | Eggers et al. |
| 6,198,394 B1 | 3/2001 | Jacobsen et al. |
| 6,200,265 B1 | 3/2001 | Walsh et al. |
| 6,203,495 B1 | 3/2001 | Bardy |
| 6,206,914 B1 | 3/2001 | Soykan et al. |
| 6,213,942 B1 | 4/2001 | Flach et al. |
| 6,221,011 B1 | 4/2001 | Bardy |
| 6,231,516 B1 | 5/2001 | Keilman et al. |
| 6,237,398 B1 | 5/2001 | Porat et al. |
| 6,238,367 B1 * | 5/2001 | Christiansen et al. ..... 604/93.01 |
| 6,254,573 B1 | 7/2001 | Haim et al. |
| 6,256,233 B1 | 7/2001 | Glass |
| 6,261,230 B1 | 7/2001 | Bardy |
| 6,264,606 B1 | 7/2001 | Ekwall et al. |
| 6,270,457 B1 | 8/2001 | Bardy |
| 6,277,072 B1 | 8/2001 | Bardy |
| 6,277,078 B1 | 8/2001 | Porat et al. |
| 6,280,380 B1 | 8/2001 | Bardy |
| 6,296,630 B1 | 10/2001 | Altman et al. |
| 6,298,272 B1 | 10/2001 | Peterfeso et al. |
| 6,309,370 B1 | 10/2001 | Haim et al. |
| 6,312,378 B1 | 11/2001 | Bardy |
| 6,331,160 B1 | 12/2001 | Bardy |
| 6,336,903 B1 | 1/2002 | Bardy |
| 6,358,202 B1 | 3/2002 | Arent |
| 6,358,203 B2 | 3/2002 | Bardy |
| 6,361,522 B1 | 3/2002 | Scheiner et al. |
| 6,361,780 B1 | 3/2002 | Ley et al. |
| 6,368,284 B1 | 4/2002 | Bardy |
| 6,398,728 B1 | 6/2002 | Bardy |
| 6,411,840 B1 | 6/2002 | Bardy |
| 6,424,847 B1 | 7/2002 | Mastrototaro et al. |
| 6,440,066 B1 | 8/2002 | Bardy |
| 6,442,413 B1 | 8/2002 | Silver |
| 6,443,949 B2 | 9/2002 | Altman |
| 6,453,195 B1 | 9/2002 | Thompson |
| 6,459,917 B1 | 10/2002 | Gowda et al. |
| 6,459,929 B1 | 10/2002 | Hopper et al. |
| 6,468,263 B1 | 10/2002 | Fischell et al. |
| 6,478,737 B2 | 11/2002 | Bardy |
| 6,501,983 B1 | 12/2002 | Natarajan et al. |
| 6,511,477 B2 | 1/2003 | Altman et al. |
| 6,518,245 B1 | 2/2003 | Anderson et al. |
| 6,628,985 B2 | 9/2003 | Sweeney et al. |
| 6,645,145 B1 | 11/2003 | Dreschel et al. |
| 6,648,881 B2 | 11/2003 | KenKnight et al. |
| 6,689,117 B2 | 2/2004 | Sweeney et al. |
| 6,693,133 B1 | 2/2004 | Lopaschuk et al. |
| 6,766,195 B1 | 7/2004 | Bornzin et al. |
| 6,802,811 B1 | 10/2004 | Slepian |
| 6,824,561 B2 | 11/2004 | Soykan et al. |
| 7,039,462 B2 | 5/2006 | Pastore et al. |
| 7,072,711 B2 | 7/2006 | Girouard et al. |
| 7,089,055 B2 | 8/2006 | Cates et al. |
| 7,236,821 B2 | 6/2007 | Cates et al. |
| 7,320,675 B2 | 1/2008 | Pastore et al. |
| 7,369,890 B2 | 5/2008 | Lovett |
| 7,400,931 B2 | 7/2008 | Mandrusov et al. |
| 7,567,841 B2 | 7/2009 | Chan |
| 7,596,408 B2 * | 9/2009 | Singhal et al. .................... 607/3 |
| 7,764,995 B2 | 7/2010 | Girouard et al. |
| 2001/0000802 A1 | 5/2001 | Soykan et al. |
| 2001/0051787 A1 | 12/2001 | Haller et al. |
| 2002/0013612 A1 | 1/2002 | Whitehurst |
| 2002/0026228 A1 | 2/2002 | Schauerte |
| 2002/0045809 A1 | 4/2002 | Ben-Haim |
| 2002/0087116 A1 | 7/2002 | Hartlaub |
| 2002/0095195 A1 * | 7/2002 | Mass et al. ..................... 607/60 |
| 2002/0099302 A1 | 7/2002 | Bardy |
| 2002/0099328 A1 | 7/2002 | Scheiner et al. |
| 2002/0107553 A1 | 8/2002 | Hill et al. |
| 2002/0120306 A1 | 8/2002 | Zhu et al. |

(56) References Cited

U.S. PATENT DOCUMENTS

| | | |
|---|---|---|
| 2002/0161410 A1 | 10/2002 | Kramer et al. |
| 2002/0169485 A1 | 11/2002 | Pless et al. |
| 2003/0004403 A1 | 1/2003 | Drinan et al. |
| 2003/0036773 A1 | 2/2003 | Whitehurst et al. |
| 2003/0045805 A1 | 3/2003 | Sheldon et al. |
| 2003/0060854 A1 | 3/2003 | Zhu |
| 2003/0069606 A1 | 4/2003 | Girouard et al. |
| 2003/0153952 A1 | 8/2003 | Auricchio et al. |
| 2003/0158584 A1 | 8/2003 | Cates et al. |
| 2003/0167081 A1 | 9/2003 | Zhu et al. |
| 2003/0233132 A1 | 12/2003 | Pastore et al. |
| 2004/0002739 A1 | 1/2004 | Cates et al. |
| 2004/0059391 A1 | 3/2004 | Sweeney et al. |
| 2004/0093034 A1 | 5/2004 | Girouard et al. |
| 2004/0106954 A1 | 6/2004 | Whitehurst et al. |
| 2004/0186546 A1 | 9/2004 | Mandrusov et al. |
| 2005/0043675 A1 | 2/2005 | Pastore et al. |
| 2005/0137626 A1 | 6/2005 | Pastore et al. |
| 2005/0137631 A1 | 6/2005 | Yu et al. |
| 2005/0283197 A1 | 12/2005 | Daum et al. |
| 2005/0288721 A1 | 12/2005 | Girouard et al. |
| 2006/0041282 A1* | 2/2006 | Hornsfeldt et al. ............ 607/37 |
| 2006/0247686 A1 | 11/2006 | Girouard et al. |
| 2008/0091138 A1 | 4/2008 | Pastore et al. |
| 2010/0286592 A1 | 11/2010 | Girouard et al. |

FOREIGN PATENT DOCUMENTS

| | | |
|---|---|---|
| EP | 0467695 A2 | 1/1992 |
| EP | 0545628 A2 | 6/1993 |
| EP | 0550343 A1 | 7/1993 |
| EP | 0550344 A1 | 7/1993 |
| EP | 0674916 A2 | 10/1995 |
| EP | 1050265 A2 | 11/2000 |
| WO | WO-93/20888 A1 | 10/1993 |
| WO | WO-96/32984 A1 | 10/1996 |
| WO | WO-97/06854 A1 | 2/1997 |
| WO | WO-97/25098 A1 | 7/1997 |
| WO | WO-97/33513 A1 | 9/1997 |
| WO | WO-98/34537 A1 | 8/1998 |
| WO | WO-00/04947 A2 | 2/2000 |
| WO | WO-00/07497 A1 | 2/2000 |
| WO | WO-01/08748 A1 | 2/2001 |
| WO | WO-01/30436 A2 | 5/2001 |
| WO | WO-01/56651 A1 | 8/2001 |

OTHER PUBLICATIONS

"U.S. Appl. No. 10/862,716, Non Final Office Action mailed Dec. 14, 2006", 10 pgs.

"U.S. Appl. No. 10/862,716, Response filed Mar. 14, 2007 to Non Final Office Action mailed Dec. 14, 2006", 18 pgs.

"U.S. Appl. No. 10/862,716, Response filed Sep. 12, 2007 to Final Office Action mailed Jul. 13, 2007", 24 pgs.

"U.S. Appl. No. 10/922,650, Advisory Action mailed Feb. 19, 2008", 3 pgs.

"U.S. Appl. No. 10/922,650, Final Office Action mailed Apr. 11, 2007", 9 pgs.

"U.S. Appl. No. 10/922,650, Final Office Action mailed Nov. 28, 2007", 12 pgs.

"U.S. Appl. No. 10/922,650, Final Office Action mailed Dec. 22, 2008", 10 pgs.

"U.S. Appl. No. 10/922,650, Non Final Office Action filed Jun. 20, 2007", 10 pgs.

"U.S. Appl. No. 10/922,650, Non Final Office Action mailed Sep. 27, 2006", 8 pgs.

"U.S. Appl. No. 10/922,650, Non-Final Office Action mailed May 29, 2008", 11 pgs.

"U.S. Appl. No. 10/922,650, Notice of Allowance mailed Mar. 31, 2009", 7 pgs.

"U.S. Appl. No. 10/922,650, Response filed Jan. 25, 2007 to Non Final Office Action mailed Sep. 27, 2006", 15 pgs.

"U.S. Appl. No. 10/922,650, Response filed Jan. 28, 2008 to Final Office Action mailed Nov. 28, 2007", 17 pgs.

"U.S. Appl. No. 10/922,650, Response filed Feb. 23, 2009 to Final Office Action mailed Dec. 22, 2008", 8 pgs.

"U.S. Appl. No. 10/922,650, Response filed Mar. 28, 2008 to Final Office Action mailed Nov. 28, 2007 and Advisory Action mailed Feb. 19, 2008", 17 pgs.

"U.S. Appl. No. 10/922,650, Response filed Jun. 11, 2007 to Final Office Action mailed Apr. 11, 2007", 15 pgs.

"U.S. Appl. No. 10/922,650, Response filed Aug. 29, 2008 to Non-Final Office Action mailed May 29, 2008", 17 pgs.

"U.S. Appl. No. 10/922,650, Response filed Sep. 14, 2006 to Restriction Requirement mailed Aug. 17, 2006", 15 pgs.

"U.S. Appl. No. 10/922,650, Response filed Sep. 19, 2007 to Non Final Office Action mailed Jun. 20, 2007", 17 pgs.

"U.S. Appl. No. 10/922,650, Restriction Requirement mailed Aug. 17, 2006", 8 pgs.

* cited by examiner

METHOD AND APPARATUS FOR DELIVERING COMBINED ELECTRICAL AND DRUG THERAPIES

CROSS-REFERENCE TO RELATED APPLICATION

This application is a divisional of U.S. application Ser. No. 10/922,650, filed Aug. 20, 2004, now issued as U.S. Pat. No. 7,567,841, which is hereby incorporated by reference in its entirety.

This application is related to commonly assigned U.S. patent application Ser. No. 10/862,716, filed on Jun. 7, 2004, now issued as U.S. Pat. No. 7,764,995 U.S. patent application Ser. No. 10/742,574, filed on Dec. 19, 2003, now abandoned, U.S. patent application Ser. No. 10/645,823, filed on Aug. 21, 2003, now U.S. Pat. No. 7,320,675, U.S. patent application Ser. No. 10/435,487, filed on May 9, 2003, now U.S. Pat. No. 7,369,890, U.S. patent application Ser. No. 10/293,907, filed on Nov. 12, 2002, now U.S. Pat. No. 7,072,711, U.S. patent application Ser. No. 10/184,019, filed on Jun. 28, 2002, now U.S. Pat. No. 7,089,055, U.S. patent application Ser. No. 10/172,825, filed on Jun. 14, 2002, now U.S. Pat. No. 7,039,462, and U.S. patent application Ser. No. 10/079,056, filed on Feb. 19, 2002, now U.S. Pat. No. 7,236,821, which are hereby incorporated by reference in their entirety.

TECHNICAL FIELD

This document generally relates to cardiac rhythm management (CRM) systems and particularly, but not by way of limitation, to such a system using implantable medical devices to deliver combined electrical and drug therapies.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes the myocardium to contract at a rhythm that is too slow, too fast, and/or irregular. Such an abnormal rhythm is generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms.

Various electrical therapies are available to treat cardiac disorders such as various types of arrhythmias and heart failure. These electrical therapies, including pacing and defibrillation therapies, are delivered to various locations of the heart. Various drug therapies are also available to treat cardiac disorders. Some drugs are most efficient or effective when directly applied to the heart, such as to a cardiac region where a disorder originates.

When properly combined, electrical and drug therapies may benefit a patient to an extent beyond what is achievable by either drug therapy or electrical therapy alone. In many circumstances, the electrical and drug therapies are most effective when delivered to specific target regions. Thus, there is a need for a system to perform localized delivery of combined electrical and drug therapies.

SUMMARY

A CRM system includes an implantable medical device that delivers combined electrical and drug therapies. The implantable medical device includes a drug reservoir that is refillable after implantation.

In one embodiment, a CRM system includes an implantable medical device that includes a pulse output circuit, a drug delivery device, an implant controller, and an implantable housing. The pulse output circuit delivers electrical pulses to a heart. The drug delivery device includes a drug reservoir adapted to contain a drug and a reservoir filling port. The implant controller controls the delivery of the electrical pulses and the drug. The implantable housing contains the pulse output circuit, the drug delivery device, and the implant controller. The reservoir filling port is constructed on the implantable housing and includes a self-resealable portion that allows filling of the drug reservoir using a hollow needle.

In another embodiment, a CRM system includes an implantable pulse generator and an implantable drug delivery device fastened to the implantable pulse generator. The implantable pulse generator, which delivers electrical pulses to a heart, includes a pulse generator circuit and an implantable housing that encapsulates the pulse generator circuit. The implantable drug delivery device, which delivers a drug, includes a drug reservoir, an implantable housing, and a reservoir filling port. The drug reservoir contains the drug. The implantable housing of the implantable drug delivery device encapsulates portions of a structure for drug delivery including the drug reservoir. The reservoir filling port is constructed on the implantable housing of the implantable drug delivery device. The reservoir filling port includes a self-resealable portion that allows filling of the drug reservoir using a hollow needle. The two implantable housings are fastened to each other.

In one embodiment, a medical device assembly is provided for use with an implantable CRM device. The medical device assembly includes an implantable drug delivery device and means for fastening the implantable drug delivering device to the implantable CRM device. The implantable drug delivery device includes a drug reservoir, an implantable housing, and a reservoir filling port. The drug reservoir contains the drug. The implantable housing, which contains portions of a structure of the implantable drug delivery device including the drug reservoir, is configured to be attached to the implantable CRM device. The reservoir filling port is constructed on the implantable housing and includes a self-resealable portion that allows filling of the drug reservoir using a hollow needle.

In one embodiment, a method for making an implantable CRM system is provided. A pulse generator circuit is provided to deliver electrical pulses to one or more electrodes. A drug delivery device including a drug reservoir is also provided. The pulse generator circuit and the drug delivery device are encapsulated using an implantable housing. A self-resealable reservoir filling port is incorporated onto the implantable housing to allow filling of the drug reservoir using a hollow needle.

In one embodiment, a method for making an implantable medical device is provided. An implantable pulse generator is provided. The implantable pulse generator includes an implantable pulse generator housing. An implantable drug delivery device is also provided. The implantable drug delivery device includes a drug reservoir, an implantable drug delivery device housing, and a self-resealable reservoir filling port. The self-resealable reservoir filling port is constructed on the implantable drug delivery device housing to allow filling of the drug reservoir using a hollow needle. The implantable drug delivery device housing is fastened to the implantable pulse generator housing.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a CRM system using one or more implantable medical devices to deliver combined electrical and drug therapies to the heart. In this document, a "drug" includes one or more agents intended for use in the diagnosis, cure, mitigation, treatment, or prevention of one or more diseases. The one or more agents may be chemical, biochemical, and/or biological in nature. Such agents include, but are not limited to, agents treating an arrhythmia, agents treating heart failure, agents treating diastolic dysfunction, agents providing ischemia protection, agents reducing fibrosis, angiogenic agents, agents supporting a cell therapy, agents recruiting cells for cell therapy, and agents promoting tissue regeneration and development.

Figure 1:
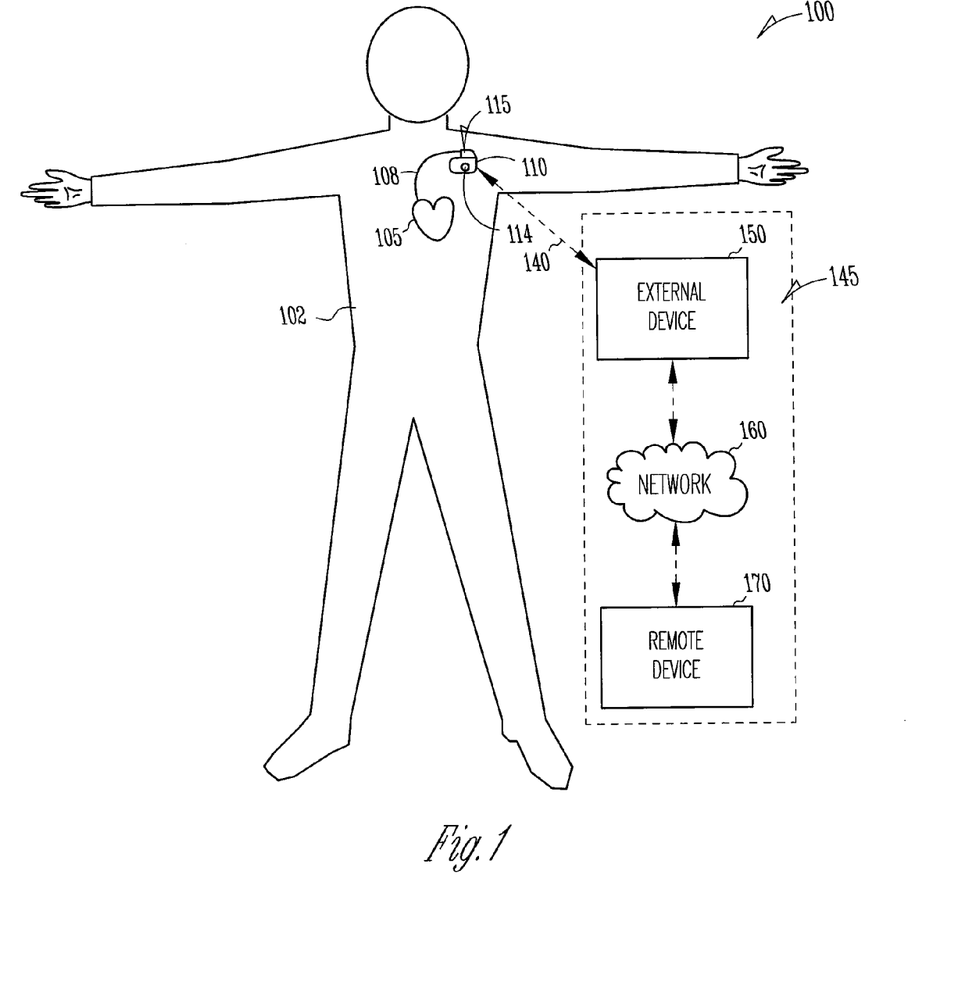
FIG. 1 is an illustration of an embodiment of a CRM system including an implantable system and an external system and portions of an environment in which the CRM system is used.

FIG. 1 is an illustration of an embodiment of a CRM system 100 and portions of an environment in which CRM system 100 is used. System 100 includes an implantable system 115 and an external system 145. Implantable system 115 includes an implantable medical device 110 and a lead system 108. In one embodiment, external system 145 includes an external device 150, a network 160, and a remote device 170. In another embodiment, external system 145 includes a medical device programmer. As shown in FIG. 1, implantable medical device 110 is implanted in a body 102 to deliver a combined electrical and drug therapy to a heart 105. A drug is stored in implantable medical device 110, which includes a drug filling port 114 to allow filling of the drug after implantation in body 102. In one embodiment, drug filling port 114 includes a self-resealable diaphragm constructed on the housing of implantable medical device 114 to allow filling of the drug using a hollow needle. Lead system 108, which provides connections between implantable medical device 110 and heart 105, includes one or more pacing and/or defibrillation leads, drug delivery leads, and/or drug delivery pacing and/or defibrillation leads. A telemetry link 140 provides for bidirectional communication between implantable medical device 110 and external device 150. Network 160 provides for bidirectional communication between external device 150 and remote device 170.

The delivery of the electrical and drug therapies is controlled by one or more of implantable medical device 110, external device 150, and remote device 170. In one embodiment, implantable medical device 110 controls the delivery of the electrical and drug therapies based on a detected signal or condition. In one embodiment, external device 150 and/or remote device 170 control the delivery of the electrical and drug therapies upon receiving an external command from a physician or other caregiver. In further embodiments, external device 150 and/or remote device 170 are capable of automated controlling the delivery of the electrical and drug therapies by processing and analyzing signals and/or conditions detected by implantable medical device 110.

Figure 2:
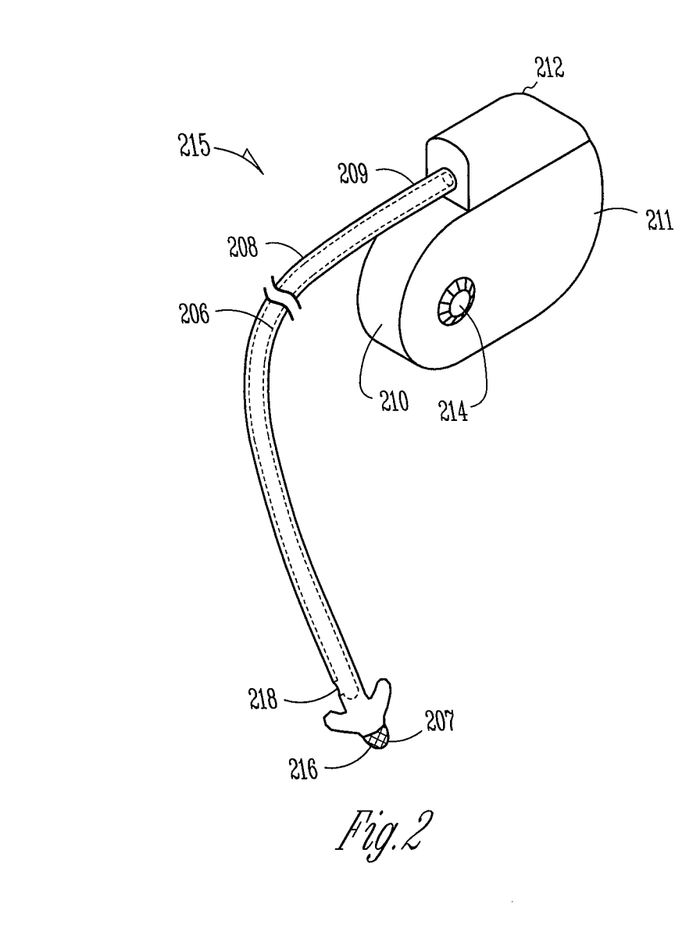
FIG. 2 is an illustration of an embodiment of the implantable system.

FIG. 2 is an illustration of an implantable system 215 being one embodiment of implantable system 115. Implantable system 215 includes an implantable medical device 210, which is an embodiment of implantable medical device 110, and a lead 208, which is a lead of lead system 108.

Implantable medical device 215 includes at least a pulse generator portion to deliver an electrical therapy and a drug delivery portion to deliver a drug therapy. The pulse generator portion includes circuitry for delivering electrical therapies including, but not being limited to, pacing therapy, cardiac resynchronization therapy (CRT), cardiac remodeling control therapy (RCT), and cardioversion/defibrillation therapy. The drug delivery portion includes a drug pump to deliver a drug and a drug reservoir to contain the drug. Implantable medical device 210 includes a can 211 and a header 212 attached to can 211. Can 211 is a hermetically sealed implantable housing encapsulating portions of the circuitry and other components of the pulse generator and drug delivery portions. Header 212 includes a connector providing for connection between lead 208 and implantable medical device 210. Implantable medical device 210 includes a reservoir filling port 214 to allow filling of the drug reservoir through a hollow needle. Reservoir filing port 214, which is an embodiment of drug filing port 114, is constructed on can 211 and includes a self-resealable diaphragm that is punctured by the hollow needle for access to the drug reservoir and self-resealed when the hollow needle is pulled out.

In one embodiment, as illustrated in FIG. 2, lead 208 is a drug delivery pacing lead, i.e., a drug delivery lead with at least one pacing electrode. Lead 208 includes a proximal end 209 and a distal end 207. Proximal end 209 is connected to implantable medical device 210 at header 212. Lead 208 includes a drug delivery port 218. In one embodiment, as illustrated in FIG. 2, drug delivery port 218 is near distal end 207. In another embodiment, drug delivery port 218 is in another location along lead 208, away from distal end 207. A lumen 206 extends within lead 208 from proximal end 209 to drug delivery port 218. Lumen 206 allows passage of the drug from the drug delivery portion of implantable medical device 210 to drug delivery port 218. In one embodiment, drug delivery port 218 is an opening through which the drug follows out of lumen 206. In another embodiment, drug delivery port 218 is made of a porous material such as a porous polymer for controlling the speed of drug release. In one embodiment, as illustrated in FIG. 2, lead 208 is a unipolar pacing lead including a tip electrode 216 at distal end 207. Pacing pulses are delivered to heart 105 through tip electrode 216 and can 211, which is used as another electrode. In addition to passing the drug, lumen 206 is also configured to accommodate a portion of a guidewire for implanting lead 208. In one embodiment, lead 208 is an epicardial lead with distal end 207 configured for epicardial placement. In another embodiment, lead 208 is an endocardial lead with distal end 207 configured for endocardial placement.

Figure 3:
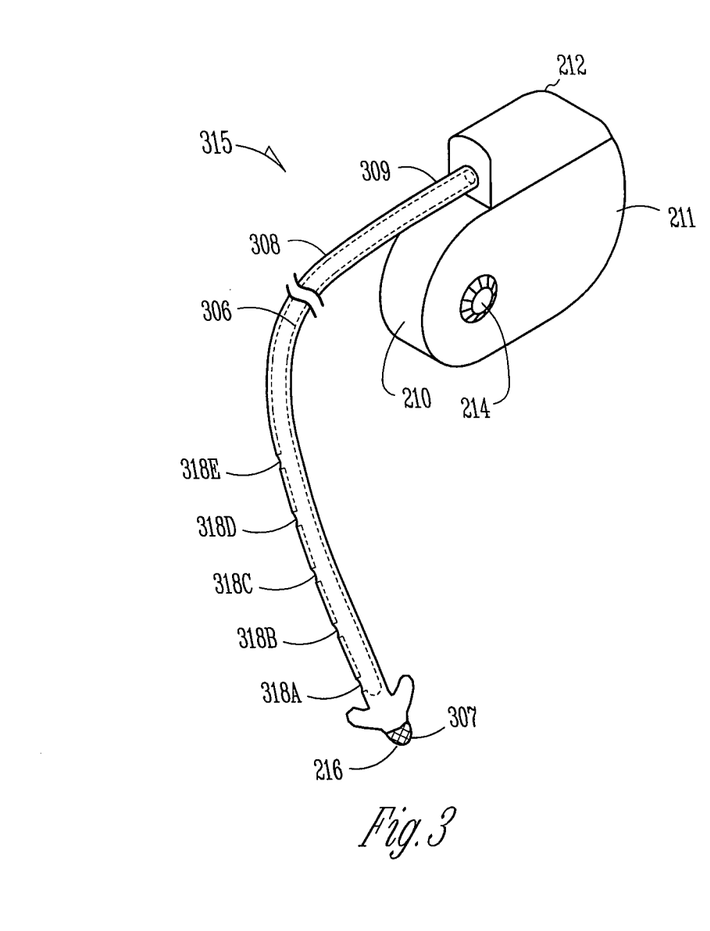
FIG. 3 is an illustration of another embodiment of the implantable system.

FIG. 3 is an illustration of an implantable system 315 being another embodiment of implantable system 115. Implantable system 315 includes implantable medical device 210 and a drug delivery pacing lead 308. Lead 308 is a lead of lead system 108 and includes a proximal end 309 and a distal end 307. Proximal end 308 is connected to implantable medical device 210 at header 212. In additional to the features of lead 208, lead 308 includes multiple drug delivery ports 318A-E. A lumen 306 extends within lead 308 from proximal end 309 to each of drug delivery ports 318A-E. Lumen 306 allows passage of the drug from the drug delivery portion of implantable medical device 210 to the each of drug delivery ports 318A-E. The number and distribution of the drug delivery ports as illustrated in FIG. 3 are for illustrative purpose only. The actual number and distribution of the drug delivery ports are determined based on the therapeutic needs, including the need and circumstances of each individual patient. In one embodiment, drug delivery ports 318A-E includes one or more drug delivery ports each being an opening through which the drug follows out of lumen 306. In another embodiment, drug delivery ports 318A-E includes one or more drug delivery ports each made of a porous material such as a porous polymer for controlling the speed of drug release.

Figure 4:
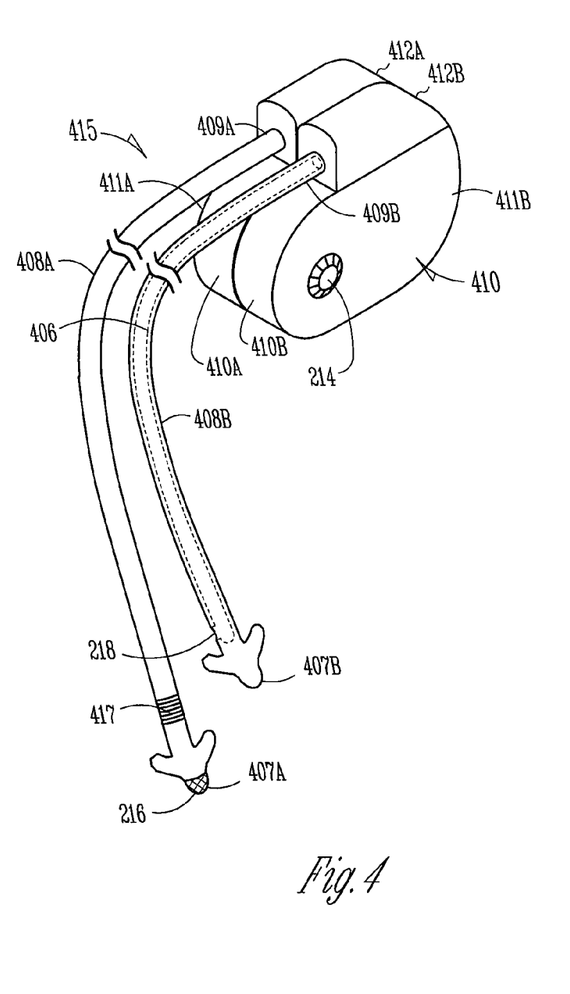
FIG. 4 is an illustration of another embodiment of the implantable system.

FIG. 4 is an illustration of an implantable system 415 being another embodiment of implantable system 115. Implantable system 415 includes an implantable medical device 410 being another embodiment of implantable medical device 110. Implantable medical device 410 includes an implantable pulse generator 410A and an implantable drug delivery device 410B, which are fastened to each other to form a single implantable device. Examples of implantable pulse generator 410A include, but are not limited to, a pacemaker, a CRT device, an RCT device, a cardioverter/defibrillator, and a pacemaker-cardioverter/defibrillator. Leads 408A and 408B are leads of lead system 108.

Implantable pulse generator 410A includes a can 411A and a header 412A attached to can 411A. Can 411A is a hermetically sealed implantable housing encapsulating portions of the circuitry and other components of implantable pulse generator 410A. Header 412A includes a connector providing for connection between a pacing lead 408A and implantable pulse generator 410A. Implantable drug delivery device 410B includes a can 411B and a header 412B attached to can 411B. Can 411B is another hermetically sealed implantable housing encapsulating portions of the circuitry and other components of implantable drug delivery device 410B. Header 412B includes a connector providing for connection between drug delivery lead 408B and implantable drug delivery device 410B. Implantable drug delivery device 410B includes a drug reservoir and reservoir filling port 214 to allow filling of the drug reservoir through a hollow needle. Reservoir filing port 214 is constructed on can 411B and includes a self-resealable portion that is punctured by the hollow needle and self-resealed when the hollow needle is pulled out during a reservoir filling.

In one embodiment, implantable pulse generator 410A and implantable drug delivery device 410B are fastened to each other by gluing can 411A and can 411B together with a biocompatible adhesive in the manner shown in FIG. 4. In a further embodiment, header 412A and header 412B are also glued together. In alternative embodiments, implantable pulse generator 410A and implantable drug delivery device 410B are fastened to each other by welding, bracing, soldering, or any other means for making implantable pulse generator 410A and implantable drug delivery device 410B permanently attached to each other. In one embodiment, implantable pulse generator 410A and implantable drug delivery device 410B have approximately identical major contours. They are aligned and then fastened to form implantable medical device 410.

In one embodiment, implantable drug delivery device 410B is provided for adding drug delivery function to an implantable CRM device that is an existing product or a product developed independently from any implantable drug delivery device. In one specific embodiment, a unit of implantable drug delivery device 410B and means for fastening it to the implantable CRM device are provided as an assembly to the physician or other caregiver. Example of the means for fastening includes, but is not limited to, a medical grade adhesive for gluing the unit of implantable drug delivery device 410B to the implantable CRM device. In a further embodiment, the assembly also includes one or more drug delivery leads required for adding the drug delivery function.

In one embodiment, as illustrated in FIG. 4, lead 408A is a bipolar pacing lead that includes a proximal end 409A and a distal end 407A. Proximal end 409A is connected to implantable pulse generator 410A. In addition to tip electrode 216, lead 408A includes a ring electrode 417 near distal end 216. Pacing pulses are delivered through a pair of electrodes being one of electrodes 216 and 417, tip electrode 216 and can 411A, and ring electrode 417 and can 411A. In one embodiment, lead 408A is an epicardial lead with distal end 407A configured for epicardial placement. In another embodiment, lead 408A is an endocardial lead with distal end 407A configured for endocardial placement.

Lead 408B is a drug delivery lead that includes a proximal end 409B and a distal end 407B. Proximal end 409B is connected to implantable drug delivery device 410B. Lead 408B includes a drug delivery port 218. In one embodiment, as illustrated in FIG. 4, drug delivery port 218 is near distal end 407B. In another embodiment, drug delivery port 218 is in another location along lead 408B, away from distal end 407B. A lumen 406 extends within lead 408B from proximal end 409B to drug delivery port 218. Lumen 406 allows passage of the drug from the drug delivery portion of implantable drug delivery device 410B to drug delivery port 218. In one embodiment, lead 408B is an epicardial lead with distal end 407B configured for epicardial placement. In another embodiment, lead 408B is an endocardial lead with distal end 407B configured for endocardial placement.

Figure 5:
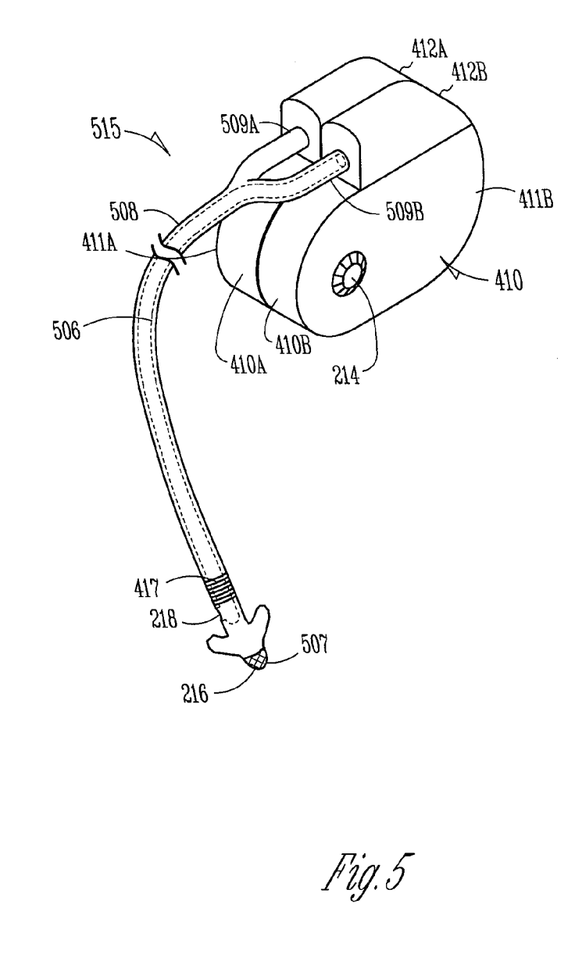
FIG. 5 is an illustration of another embodiment of the implantable system.

FIG. 5 is an illustration of an implantable system 515 being another embodiment of implantable system 115. Implantable system 515 includes implantable medical device 410 and a drug delivery pacing lead 508 being a lead of lead system 108. Lead 508 is a branched drug delivery pacing lead that includes proximal ends 509A and 509B and a distal end 507. Proximal end 509A is connected to implantable pulse generator 410A. Proximal end 409B is connected to implantable drug delivery device 410B. A lumen 506 extends within lead 408 from proximal end 509B to drug delivery port 218. In one embodiment, as illustrated in FIG. 5, drug delivery port 218 is near distal end 507. In another embodiment, drug delivery port 218 is in another location along lead 508, away from distal end 507. Lumen 506 allows passage of the drug from implantable drug delivery device 410B to drug delivery port 218. In one embodiment, as illustrated in FIG. 5, lead 508 is a bipolar pacing lead including tip electrode 216 at distal end 507 and ring electrode 417 near distal end 507. Pacing pulses are delivered through a pair of electrodes including one of electrodes 216 and 417, tip electrode 216 and can 411A, and ring electrode 417 and can 411A. In addition to passing the drug, lumen 506 is also configured to accommodate a portion of a guidewire for implanting lead 508. In one embodiment, lead 508 is an epicardial lead with distal end 507 configured for epicardial placement. In another embodiment, lead 508 is an endocardial lead with distal end 507 configured for endocardial placement.

The number and types of leads connected to implantable medical device 110, including its embodiments such as implantable medical devices 210 and 410, depend on the patient's therapeutic needs and the intended use of the implantable system. In various embodiments, implantable medical devices 210 and 410 may each include additional connectors to accommodate more lead than those illustrated in FIGS. 2-5. The leads and implantable devices illustrated in FIGS. 2-5 may be combined differently when appropriate to form additional embodiments of implantable system 115. The features on each lead as illustrated in FIGS. 2-5 may be combined to form additional embodiments of leads in lead system 108. For example, a ring electrode may be incorporated near distal end 207 of lead 208 to form a drug delivery bipolar pacing lead, and drug delivery ports 318A-E may be incorporated into lead 408B to form a drug delivery lead with multiple drug delivery ports. In embodiments in which implantable medical device 110 includes a cardioverter/defibrillator circuit, one or more defibrillation electrodes are incorporated into one or more leads of lead system 108. In general, lead system 108 includes one or more of (i) drug delivery lead (lead with one or more drug delivery ports), (ii) pacing lead (lead with one or more pacing electrodes), (iii) defibrillation lead (lead with one or more defibrillation electrodes), (iv) pacing/defibrillation lead (lead with one or more pacing electrodes and one or more defibrillation electrodes), (v) drug delivery pacing lead (lead with one or more pacing electrodes and one or more drug delivery ports), (vi) drug delivery defibrillation lead (lead with one or more defibrillation electrodes and one or more drug delivery ports), and (vii) drug delivery pacing/defibrillation lead (lead with one or more pacing electrodes, one or more defibrillation electrodes, and one or more drug delivery ports). The pacing and defibrillation electrodes are also used as electrodes for electrogram sensing.

Figure 6:
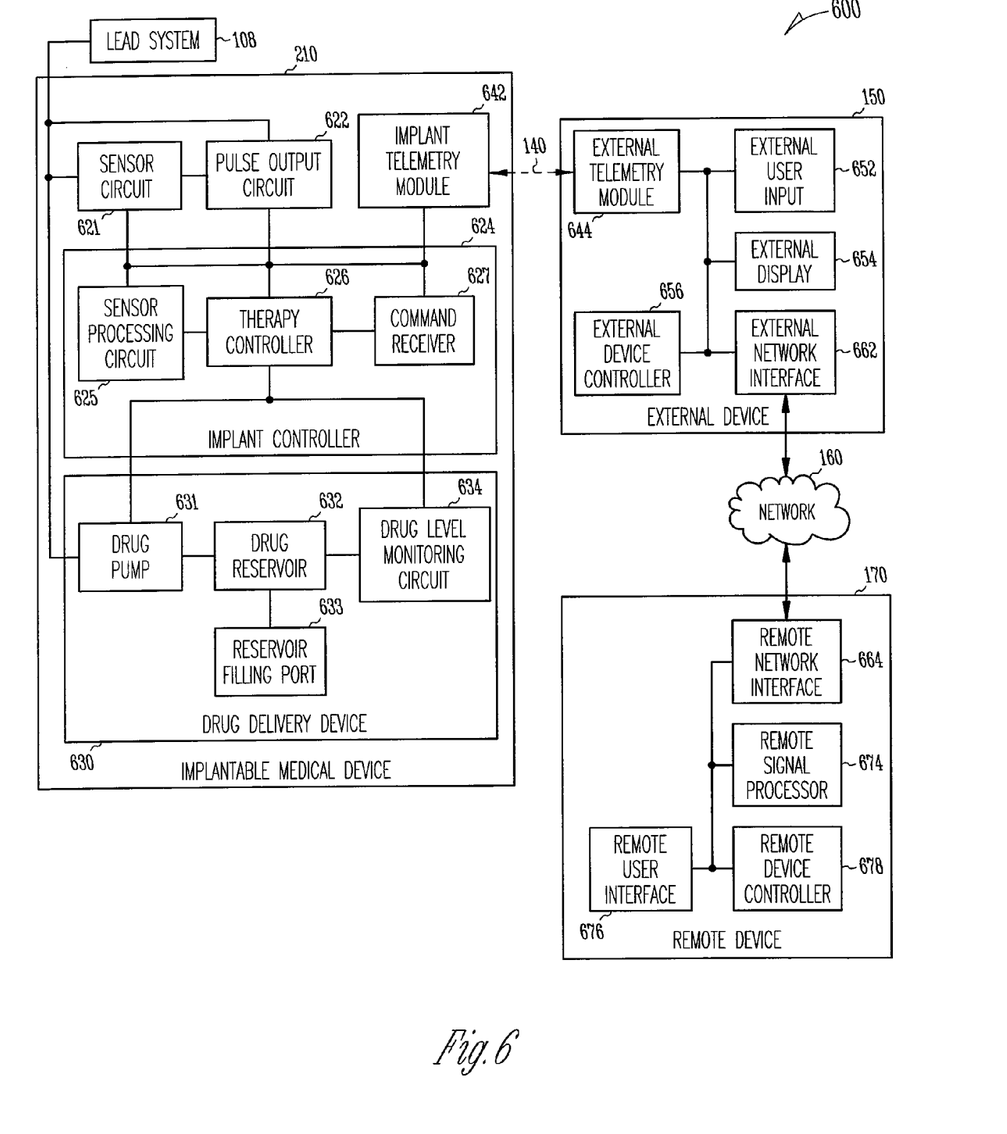
FIG. 6 is a block diagram illustrating one embodiment of the circuit of portions of the CRM system.

FIG. 6 is a block diagram illustrating one embodiment of the circuit of portions of a CRM system 600. CRM system 600 is an embodiment of CRM system 100 and includes an implantable system and an external system. The implantable system includes implantable medical device 210 and lead system 108. The external system includes external device 150, network 160, and remote device 170.

Implantable medical device 210 includes a sensor circuit 621, a pulse output circuit 622, an implant controller 624, a drug delivery device 630, and an implant telemetry module 642. Implant telemetry module 642 provides for a telemetry interface allowing implantable medical device 210 to communicate with external device 150 via telemetry link 140.

Sensor circuit 621 senses one or more signals each indicative of a need to deliver at least one of the electrical and drug therapies. In one embodiment, sensor circuit 621 includes an electrogram sensing amplifier circuit to sense one or more electrograms. In a further embodiment, sensor circuit 621 includes one or more implantable sensors to sense additional physiological signals. In one embodiment, the one or more implantable sensors include at least one sensor housed in can 211 of implantable medical device 210. In another embodiment, the one or more implantable sensors include at least one sensor incorporated into a lead of lead system 108.

Pulse output circuit 622 delivers electrical pulses to the heart through electrodes of lead system 108. Pulse output circuit 622 includes one or more of a pacing circuit to deliver pacing pulses and a cardioversion/defibrillation circuit to deliver cardioversion/defibrillation shocks.

Implant controller 624 controls the operation of implantable medical device 210. Implant controller 624 includes a sensor processing circuit 625, a therapy controller 626, and a command receiver 627. Sensor processing circuit 625 processes the one or more signals sensed by sensor circuit 621 to produce diagnostic and/or therapeutic control signals. Command receiver 627 receives the external command entered by the physician or other caregiver and sent from the external system through implant telemetry module 642 and telemetry link 140. Therapy controller 626 controls the delivery of the electrical and drug therapies based on the therapeutic control signals and the external command.

Therapy controller 626 includes an electrical therapy controller and a drug therapy controller. The electrical therapy controller includes a pacing algorithm execution circuit to control the delivery of pacing pulses by executing a pacing algorithm. In one embodiment, the pacing algorithm execution circuit executes a pacing algorithm designed to enhance one or more effects of the drug therapy. In a specific embodiment, the pacing algorithm execution circuit includes a CRT pacing algorithm execution circuit to execute a CRT pacing algorithm. The CRT provides for an approximately optimal hemodynamic performance. In one embodiment, a CRT pacing algorithm is executed with one or more pacing parameters approximately optimized to maximize a measure of hemodynamic performance. In another specific embodiment, the pacing algorithm execution circuit includes an RCT pacing algorithm execution circuit to execute an RCT pacing algorithm. The RCT alters the cardiac remodeling process, for example, by redistributing the workload and stress on the ventricular walls. In a further specific embodiment, the pacing algorithm execution module executes a dynamic pacing algorithm that dynamically adjusts pacing parameters, such as alternating between the CRT and RCT, based on a patient's changing needs and conditions. The drug therapy controller produces a drug delivery signal to direct a drug release from drug delivery device 630. In one embodiment, drug delivery device 630 releases the drug while the drug delivery signal is present. In another embodiment, drug delivery device 630 starts releasing the drug upon receiving a drug delivery signal and stops releasing the drug upon receiving another drug delivery signal. In another embodiment, drug delivery device 630 releases the drug for a predetermined time period upon receiving the drug delivery signal. In a specific embodiment, the predetermined time period is specified by the drug delivery signal.

In one embodiment, the electrical and drug therapies are closed-loop controlled by using one or more sensors sensing the need and the effect of the electrical and drug therapies. Sensor processing circuit 625 processes the signal sensed by sensor circuit 621 for therapy controller 626 to determine whether to start, stop, or adjust the electrical and/or drug therapies. In one embodiment, sensor processing circuit 625 produces the therapeutic control signals as one or more parameters based on the one or more signals sensed by sensor circuit 621. In one embodiment, sensor processing circuit 625 includes an event detector to detect one or more predetermined events indicative of a need to start, stop, or adjust the electrical and/or drug therapies. The one or more parameters produced by sensor processing circuit 625 include parameters indicative of the detection of the event and/or measured parameters associated with the detected event. In one specific embodiment, the event includes an abnormal condition. In one embodiment, sensor circuit 621 includes a plurality of sensors to sense multiple signals used by therapy controller 626 to determine whether to start, stop, or adjust the electrical and/or drug therapies. Each of the multiple signals may be used by therapy controller 626 to control the drug therapy, the electrical therapy, or coordinated electrical and drug therapies. The one or more signals sensed by sensor circuit 621 include, but are not limited to, one or more of an electrogram indicative of arrhythmia and/or heart rate variability, a physiological signal indicative of ischemia, a metabolic signal indicative of a cardiac metabolic level (rate of metabolism of cardiac cells), a thoracic impedance, an intracardiac or intravascular pressure, a cardiac output or stroke volume, a neural signal indicative of activities of the autonomic nervous system, a signal indicative of renal function, a signal indicative of heart sounds, a signal indicative of respiratory sounds, a signal indicative of a strain of myocardial tissue, and a temperature signal. Examples of such signals and their use in controlling electrical and drug therapies are discussed in U.S. patent application Ser. No. 10/742,574, U.S. patent application Ser. No. 10/788,906, and U.S. patent application Ser. No. 10/862,716, all assigned to Cardiac Pacemakers, Inc., which are hereby incorporated by reference in their entirety. Other methods and sensors for directly or indirectly detecting an event or condition demanding the start, stop, or adjustment of the electrical and/or therapies are also usable by system 100.

Drug delivery device 630 includes a drug pump 631, a drug reservoir 632, a reservoir filling port 633, and a drug level monitoring circuit 634. Drug pump 631 draws the drug from drug reservoir 632 and pumps the drug into the lumen of a drug delivery lead (such as one of the drug delivery leads discussed above) to deliver the drug by releasing it from one or more drug delivery ports in lead system 108. Drug reservoir 632 contains the drug. Reservoir filling port 633 is connected to drug reservoir 632 to allow filling of the drug reservoir. In one embodiment, reservoir filling port 633 is constructed on an implantable housing of the implantable medical device 210, such as illustrated as reservoir filing port 214 in FIGS. 2-5. Drug level monitoring circuit 634 monitors the level of the drug in drug reservoir 632. In one embodiment, when the level of the drug in drug reservoir 632 falls below a predetermined minimum level, drug level monitoring circuit 634 produces a drug level alert signal to be transmitted to the external system through telemetry link 140. If deemed necessary, the physician or other caregiver refills drug reservoir 632 by injecting the drug through reservoir filling port 633 using a syringe and a hollow needle.

Depending on the therapeutic functions and intended use of implantable medical device 210, lead system 108 includes one or more of drug delivery lead, pacing lead, defibrillation lead, pacing/defibrillation lead, drug delivery pacing lead, drug delivery defibrillation lead, and drug delivery pacing/defibrillation lead. In one embodiment, lead system 108 includes at least one drug delivery lead for intracardiac delivery of the drug. In another embodiment, lead system 108 includes at least one drug delivery lead for epicardial delivery of the drug. In another embodiment, lead system 108 includes at least one drug delivery lead for intravascular delivery of the drug. In one embodiment, lead system 108 further include one or more sensors of sensor circuit 621 incorporated into one or more leads. In one specific embodiment, sensor circuit 621 includes a pressure sensor housed within implantable medical device 210. Lead system 108 includes at least one lead having two or more lumens. One of the lumens is configured to allow intracardiac pressure sensing.

In one embodiment, implantable medical device 210 is capable of delivering a plurality of drugs, with the delivery of each drug individually controllable. In this embodiment, drug reservoir 632 includes a plurality of drug compartments each containing one drug. Drug pump 631 includes a plurality of pumps each draws drug from one compartment of drug reservoir 632 to deliver the drug in response to a drug delivery signal produced by therapy controller 626. The drug delivery signal is specific to each drug to be delivered. In one embodiment, the drugs are delivered to the same location, with the timing of delivery individually controllable for each drug. In another embodiment, lead system 108 includes a plurality of drug delivery leads for delivering different drugs to different locations.

External device 150 includes an external user input 652, an external display 654, an external device controller 656, an external telemetry module 644, and an external network interface 662. In one embodiment, external user input 652 receives the external command controlling the electrical and/or drug therapies from the physician or other caregiver. In a further embodiment, external user input 652 also receives other commands or instructions to control the operation implantable medical device 210. In one embodiment, the external command controlling the electrical and drug therapies is sent from remote device 170. External device 150 relays the external command to implantable medical device 210. In one specific embodiment, the external command includes a drug delivery command. External device 150 transmits the drug delivery command to implantable medical device 210 to result in a production of the drug delivery signal by the drug delivery controller of therapy controller 626. External telemetry module 644 provides for a telemetry interface allowing external device 150 to communicate with implantable medical device 210 via telemetry link 140. External network interface 662 provides for a network interface allowing external device 150 to communicate with remote device 170 via network 160.

Telemetry link 140 is a wireless bidirectional data transmission link supported by implant telemetry module 642 and external telemetry module 644. In one embodiment, telemetry link 140 is an inductive couple formed when two coils—one connected to implant telemetry module 642 and the other connected to external telemetry module 644—are placed near each other. In another embodiment, telemetry link 140 is a far-field radio-frequency telemetry link allowing implantable medical device 210 and external device 150 to communicate over a telemetry range that is at least ten feet.

Remote device 170 includes a remote signal processor 674, a remote user interface 676, a remote device controller 678, and a remote network interface 664. By executing one or more predetermined algorithms, remote signal processor 674 processes signals transmitted from implantable medical device 210 and external device 150. In one embodiment, remote signal processor 674 analyzes signals acquired by implantable medical device 210 and transmitted to remote device 170, such as the one or more signals sensed by sensor circuit 621, to determine the need for starting, stopping, or adjusting the electrical and/or drug therapies. Remote user interface 676 includes a remote user input to allow the physician or other caregiver to enter the external command from a remote location. In one embodiment, remote user interface 676 receives the drug level alert signal generated by drug level monitoring circuit 634 and informs the physician or other caregiver that the drug level in drug reservoir is low. Remote device controller 678 controls the overall operation of remote device 170. In one embodiment, remote device controller 678 generates commands controlling implantable medical device 210 and/or external device 150 based on the received signals and the external command. In one embodiment, remote device controller 678 executes an automatic algorithm to control the electrical and/or drug therapies, such as when the physician or other caregiver is not immediately available. Remote network interface 664 provides for an interface allowing communication between remote device 170 and external device 150 via network 160.

Network 160 provides long distance bi-directional communication between external device 150 and remote device 170. It allows management of multiple implantable systems, each implanted in a different patient, from a central facility. In one embodiment, this allows prompt response by a physician or other caregiver at the central facility as demanded by the condition of a patient. In one embodiment, network 160 is based on a wireless communications system. In another embodiment, network 160 is based on a wired communications system. In one embodiment, network 160 utilizes portions of a standard communications system such as the Internet, a telephone system, or a radio frequency telemetry system.

Figure 7:
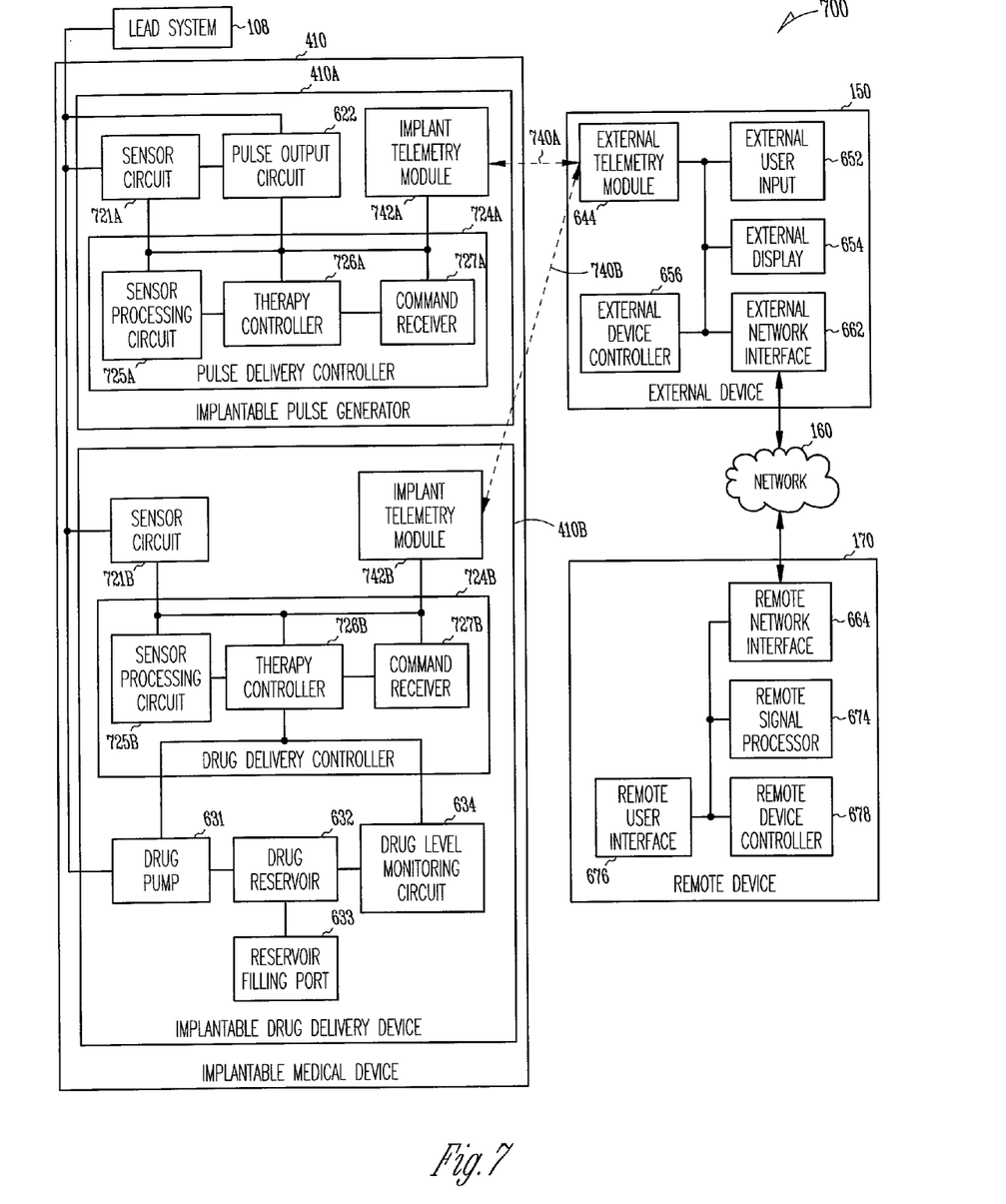
FIG. 7 is a block diagram illustrating another embodiment of the circuit of portions of the CRM system.

FIG. 7 is a block diagram illustrating one embodiment of the circuit of portions of a CRM system 700. CRM system 700 is an embodiment of CRM system 100 and includes an implantable system and an external system. The implantable system includes implantable medical device 410 and lead system 108. Implantable medical device 410 includes implantable pulse generator 410A and implantable drug delivery device 410B, which are fastened to each other. The external system includes external device 150, network 160, and remote device 170.

Implantable pulse generator 410A includes a sensor circuit 721A, pulse output circuit 622, a pulse delivery controller 724A, and an implant telemetry module 742A. Implant telemetry module 742A provides for a telemetry interface allowing implantable pulse generator 410A to communicate with external device 150 via a telemetry link 740A.

Sensor circuit 721A senses one or more signals each indicative of a need to deliver the electrical therapy. In one embodiment, sensor circuit 721A further senses one or more signals each indicative of a need to deliver the drug therapy. These signals are transmitted to the external system via telemetry link 140 for controlling the drug therapy through the external system. In one embodiment, sensor circuit 721A includes an electrogram sensing amplifier circuit to sense one or more electrograms. In a further embodiment, sensor circuit 721A includes one or more implantable sensors to sense additional physiological signals. In one embodiment, the one or more implantable sensors include at least one sensor housed in can 411A of implantable pulse generator 410A. In another embodiment, the one or more implantable sensors include at least one sensor incorporated into a lead of lead system 108.

Pulse delivery controller 724A controls the operation of implantable pulse generator 410A. Pulse delivery controller 724A includes a sensor processing circuit 725A, a therapy controller 726A, and a command receiver 727A. Sensor processing circuit 725A processes the one or more signals sensed by sensor circuit 721A to produce diagnostic and/or therapeutic control signals, as discussed above for sensor processing circuit 625 and sensor circuit 621. Command receiver 727A receives the external command entered by the physician or other caregiver and sent from the external system through implant telemetry module 742A and telemetry link 140. Therapy controller 726A controls the delivery of the electrical therapy based on the therapeutic control signals and the external command.

Therapy controller 726A includes an electrical therapy controller. The electrical therapy controller includes a pacing algorithm execution circuit to control the delivery of pacing pulses by executing a pacing algorithm. In one embodiment, the pacing algorithm execution circuit executes a pacing algorithm designed to enhance one or more effects of the drug therapy. In a specific embodiment, the pacing algorithm execution circuit includes one or more of a CRT pacing algorithm execution circuit and an RCT pacing algorithm execution circuit. In a further specific embodiment, the pacing algorithm execution module executes a dynamic pacing algorithm that dynamically adjusts pacing parameters, such as alternating between the CRT and RCT, based on a patient's changing needs and conditions.

In one embodiment, the electrical therapy is closed-loop controlled by using one or more sensors sensing the need and the effect of the electrical and drug therapies. Sensor processing circuit 725A processes the signal sensed by sensor circuit 721A for therapy controller 726B to determine whether to start, stop, or adjust the electrical and/or drug therapies. In a further embodiment, sensor circuit 721A and sensor processing circuit 725A also senses and processes one or more signals to provide closed-loop control of the drug therapy by using one or more sensors sensing the need and the effect of the electrical and drug therapies. The signals or parameters derived from the signals are transmitted to implantable drug delivery device 410B through the external system for implantable drug delivery device 410B to determine whether to start, stop, or adjust the drug therapy. In one embodiment, sensor circuit 721A includes sensor circuit 621 or portions of it, and sensor processing circuit 725A includes sensor processing circuit 625 or portions of it.

Implantable drug delivery device 410B includes a sensor circuit 721B, a drug delivery controller 724B, drug pump 631, drug reservoir 632, reservoir filling port 633, drug level monitoring circuit 634, and an implant telemetry module 742B. Implant telemetry module 742B provides for a telemetry interface allowing implantable drug delivery device 410B to communicate with external device 150 via a telemetry link 740B.

Sensor circuit 721B senses one or more signals each indicative of a need to deliver the drug therapy. In one embodiment, sensor circuit 721B includes an electrogram sensing amplifier circuit to sense one or more electrograms. In a further embodiment, sensor circuit 721B includes one or more implantable sensors to sense additional physiological signals. In one embodiment, the one or more implantable sensors include at least one sensor housed in can 411B of implantable drug delivery device 410B. In another embodiment, the one or more implantable sensors include at least one sensor incorporated into a lead of lead system 108.

Drug delivery controller 724B controls the operation of implantable drug delivery device 410B. Drug delivery controller 724B includes a sensor processing circuit 725B, a therapy controller 726B, and a command receiver 727B. Sensor processing circuit 725B processes the one or more signals sensed by sensor circuit 721B to produce diagnostic and/or therapeutic control signals. Command receiver 727B receives an external command sent from the external system through implant telemetry module 742A and telemetry link 140. Therapy controller 726B controls the delivery of the drug therapy based on the therapeutic control signals and the external command.

Therapy controller 726B includes a drug therapy controller. The drug therapy controller produces a drug delivery signal to direct a drug release from drug pump 631. In one embodiment, drug pump 631 releases the drug while the drug delivery signal is present. In another embodiment, drug pump 631 starts releasing the drug upon receiving a drug delivery signal and stops releasing the drug upon receiving another drug delivery signal. In another embodiment, drug pump 631 releases the drug for a predetermined time period upon receiving the drug delivery signal. In a specific embodiment, the predetermined time period is specified by the drug delivery signal.

In one embodiment, the drug therapy is closed-loop controlled by using one or more sensors sensing the need and the effect of the electrical and drug therapies. Sensor processing circuit 725B processes the signal sensed by sensor circuit 721B for therapy controller 626 to determine whether to start, stop, or adjust the drug therapy. In one embodiment, sensor circuit 721B includes sensor circuit 621 or portions of it, and sensor processing circuit 725B includes sensor processing circuit 625 or portions of it. In one embodiment, the drug therapy is closed-loop controlled by using one or more sensors of sensor circuit 721A in implantable pulse generator 410A. Signals sensed by sensor 721A and processed by sensor processing circuit 725A are transmitted to implantable drug delivery device 410B for use by drug delivery controller 724B to determine to start, stop, or adjust the drug therapy.

Telemetry link 740A is a wireless bidirectional data transmission link supported by implant telemetry module 742A and external telemetry module 644. Telemetry link 740B is another wireless bidirectional data transmission link supported by implant telemetry module 742B and external telemetry module 644. In one embodiment, telemetry links 740A and 740B are time-sharing telemetry links that allow one of communication between implantable pulse generator 410A and external device 150 and communication between implantable drug delivery device 410B and external device 150 at one instant. In another embodiment, telemetry links 740A and 740B allows simultaneous or concurrent communications between implantable pulse generator 410A and external device 150 and between implantable drug delivery device 410B and external device 150.

Figure 8:
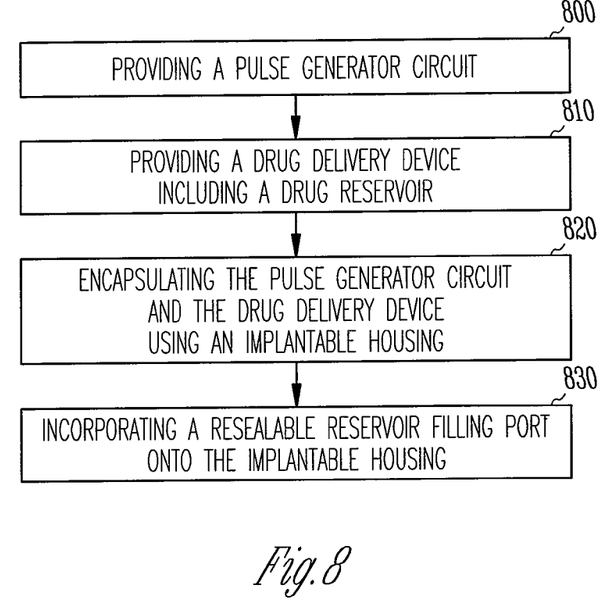
FIG. 8 is a flow chart illustrating one embodiment of a method for making a CRM system delivering combined electrical and drug therapies.

FIG. 8 is a flow chart illustrating one embodiment of a method for making a CRM system that delivers combined electrical and drug therapies. In one embodiment, the method is applied to make implantable system 215 or 315.

A pulse generator circuit is provided at 800. The pulse generator circuit includes a pulse output circuit to deliver electrical pulses to the heart through one or more leads with electrodes. Depending on the intended use of the implantable system, the pulse generator circuit includes one or more of a pacemaker circuit, a circuit for delivering a CRT, a circuit for delivering an RCT, and a cardioverter/defibrillator circuit.

A drug delivery device including a drug reservoir is provided at 810. The drug reservoir is filled with a drug to be delivered to the cardiovascular system. In one embodiment, a control circuit is provided to control the pulse generator circuit and the drug delivery device to deliver combined electrical and drug therapies. In one specific embodiment, the electrical and drug therapies are temporally coordinated. In one further embodiment, a sensor circuit is provided to sense one or more signals each indicative of a cardiac function. A feedback control circuit is provided to control the delivery of the electrical pulses and the drug therapies based on at least the sensed one or more signals.

The pulse generator circuit and the drug delivery device are encapsulated using an implantable housing at 820 to form an implantable medical device. In one embodiment, the implantable housing includes a hermetically sealed can to house the pulse generator circuit, the drug delivery device, the control circuit including the feedback control circuit, and the sensor circuit.

A self-resealable reservoir filling port is constructed on the implantable housing at 830. The self-resealable reservoir filling port includes a self-resealable diaphragm that allows filling of the drug through a hollow needle. To fill or refill the drug reservoir, the drug is drawn into a syringe with the hollow needle. The hollow needle is inserted through the self-resealable diaphragm. When the filling is completed, the diaphragm reseals itself as the hollow needle is pulled out.

In addition to the implantable medical device, at least one drug delivery lead is provided. The lead is to be connected to the implantable medical device. In one embodiment, an implantable lead with one or more electrodes is provided to allow delivery of the electrical pulses. A lumen is provided within the implantable lead for passing the drug from the drug delivery device to one or more drug delivery ports incorporated into the implantable lead. In another embodiment, an implantable pacing lead with one or more electrodes is provided to allow delivery of the electrical pulses, and a separate implantable drug delivery lead is provided to allow delivery of the drug. The drug delivery lead includes a lumen for passing the drug from the drug delivery device to one or more drug delivery ports incorporated into the implantable drug delivery lead.

Figure 9:
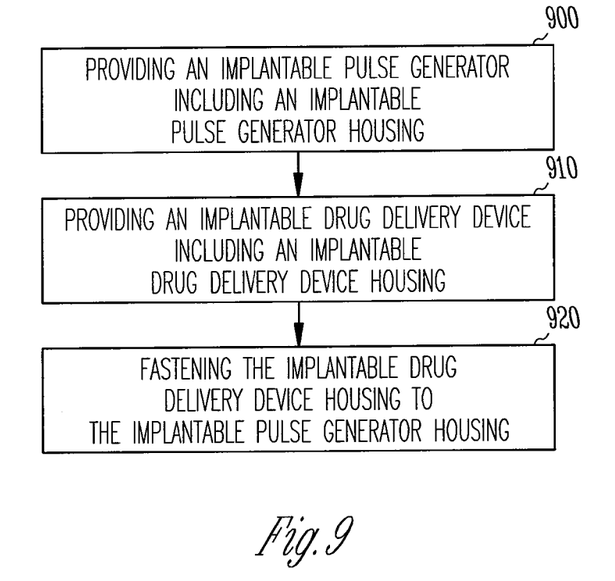
FIG. 9 is a flow chart illustrating one embodiment of another method for making a CRM system delivering combined electrical and drug therapies.

FIG. 9 is a flow chart illustrating one embodiment of another method for making a CRM system delivering combined electrical and drug therapies. In one embodiment, the method is applied to make implantable system 415 or 515.

An implantable pulse generator is provided at 900. The implantable pulse generator includes an implantable pulse generator housing such as a hermetically sealed can. Examples of the implantable pulse generator include, but are not limited to, an implantable pacemaker, an implantable CRT device, an implantable RCT device, and an implantable cardioverter/defibrillator.

An implantable drug delivery device is provided at 910. The implantable drug delivery device includes a drug reservoir, a self-resealable reservoir filling port, and an implantable drug delivery device housing such as a hermetically sealed can. The self-resealable reservoir filling port is constructed on the implantable drug delivery device housing to allow filling of the drug reservoir through a hollow needle.

The implantable pulse generator housing and the implantable drug delivery device housing are fastened to each other at 920 to form an implantable medical device. In one embodiment, implantable housing having approximately identical major contours are provided for use as the implantable pulse generator housing and the implantable drug delivery device housing. In one embodiment, the implantable drug delivery device housing is glued to the implantable pulse generator housing a biocompatible adhesive. In another embodiment, the implantable drug delivery device housing is welded to the implantable pulse generator housing. In another embodiment, the implantable drug delivery device housing is braced to the implantable pulse generator housing. In general, the implantable drug delivery device housing is configured for attachment to the implantable pulse generator housing. The implantable drug delivery device can be fastened to the implantable pulse generator using any method for permanently attaching the implantable drug delivery device housing to the implantable pulse generator housing.

In addition to the implantable medical device, one or more pacing leads, defibrillation leads, pacing/defibrillation leads, drug delivery leads, drug delivery pacing leads, drug delivery defibrillation leads, and/or drug delivery pacing/defibrillation leads are provided. Depending on the intended use of the implantable system, one or more of such leads are selected to be connected to the implantable pulse generator and the implantable drug delivery device.

It is to be understood that the above detailed description is intended to be illustrative, and not restrictive. Although the present therapy is described in the context of cardiac therapy as a specific example, it is understood that many other applications are possible. Combined electrical and drug therapies can be used to treat conditions other than cardiac disorders. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
    an implantable pulse generator to deliver electrical pulses, the implantable pulse generator including:
        a pulse generator circuit including:
            a pulse output circuit to deliver cardiac pacing pulses;
            a sensor circuit to sense one or more signals indicative of a need for and an effect of the delivery of the electrical pulses and the delivery of the drug; and
            an implant controller including a sensor processing circuit adapted to process the one or more signals and a therapy controller adapted to control the delivery of the cardiac pacing pulses and the delivery of the drug using the processed one or more signals; and
    a first implantable housing configured to encapsulate the pulse generator circuit; and
    an implantable drug delivery device to deliver a drug, the implantable drug delivery device including:
        a drug reservoir to contain the drug;
        a second implantable housing configured to encapsulate portions of a structure of the implantable drug delivery device including the drug reservoir, the second implantable housing fastened to the first implantable housing; and
        a reservoir filling port constructed on the second implantable housing, the reservoir filling port including a self-resealable portion adapted to allow filling of the drug reservoir through a hollow needle,
    wherein the therapy controller is adapted to control the delivery of the cardiac pacing pulses by alternately executing a cardiac resynchronization therapy (CRT) algorithm adapted to maximize a measure of hemodynamic performance and a remodeling control (RCT) algorithm adapted to alter a cardiac remodeling process.

* * * * *